United States Patent [19]

Ohnishi et al.

[11] Patent Number: 5,684,061
[45] Date of Patent: Nov. 4, 1997

[54] BONE INDUCING MATERIAL

[75] Inventors: Toshiyuki Ohnishi, 1584, Inbe, Bizen-shi, Okayama 705; Nobuhiro Moriyama, Iwaki, both of Japan

[73] Assignees: Kureha Chemical Industry Co., Ltd., Tokyo; Yasunari Uchida, Fukuoka; Toshiyuki Ohnishi, Okayama, all of Japan

[21] Appl. No.: 718,991

[22] Filed: Sep. 26, 1996

Related U.S. Application Data

[63] Continuation of Ser. No. 267,009, Jun. 2, 1994, abandoned.

[30] Foreign Application Priority Data

Jun. 2, 1993 [JP] Japan ................................. 5-156193

[51] Int. Cl.$^6$ .............................. A61F 2/28; C08G 63/06; C08F 12/20
[52] U.S. Cl. .................... 523/114; 523/105; 523/300; 521/145; 521/182; 524/436; 528/354; 528/361; 310/800; 310/367; 310/363; 623/16
[58] Field of Search ................................. 523/105, 114, 523/300; 524/436; 310/800, 367, 363; 623/16; 521/145, 182; 528/354, 361

[56] References Cited

U.S. PATENT DOCUMENTS

| | | | |
|---|---|---|---|
| 4,578,384 | 3/1986 | Hollinger | 424/22 |
| 4,777,153 | 10/1988 | Sonuparlak et al. | 264/66 |
| 4,828,705 | 5/1989 | Thakore et al. | 210/636 |
| 4,904,394 | 2/1990 | Clarke et al. | 210/739 |
| 5,250,584 | 10/1993 | Ikada et al. | 523/114 |

FOREIGN PATENT DOCUMENTS

| | | |
|---|---|---|
| A2161080 | 7/1985 | United Kingdom . |
| WO88 06866 | 9/1988 | WIPO . |

OTHER PUBLICATIONS

Japanese Journal of Applied Physics, vol. 14, No. 12, 1975, Tokyo, pp. 2079–2080, E. Fukada "Callus Formation by Electret".

Patent Abstracts of Japan, vol. 13, No. 546 (C–661) 6 Dec. 1989, re JP–A–01 223 954 (Daikin Ind. Ltd) 7 Sep. 1989.

*Primary Examiner*—Andrew E. C. Merriam
*Attorney, Agent, or Firm*—Sughrue, Mion, Zinn, Macpeak & Seas, PLLC

[57] ABSTRACT

A bone inducing material comprising a piezoelectric porous membrane having through-holes of an average pore size of about 0.1 to 5 μm is disclosed. When the bone inducing material according to the present invention is used, bone is rapidly regenerated, and new formation of bone occurs. The bone inducing material is particularly useful in the dental field, for example, for treatment of periodontal diseases by GTR method.

8 Claims, 4 Drawing Sheets

BONE INDUCING MATERIAL

This is a Continuation of application Ser. No. 08/267,009 filed Jun. 2, 1994, now abandoned.

BACKGROUND OF THE INVENTION

1. Field of the Invention

The present invention relates to a bone inducing material, more particularly, to a bone inducing material composed of a piezoelectric porous membrane having through-holes of an average diameter of 0.1 to 5 μm.

2. Description of the Related Art

Since it was found that there exists a piezoelectric phenomenon in bone, various experimental and clinical attempts to increase bone production by electrically stimulating the bone have been reported. As examples of making use of a piezoelectric sheet, in particular, there Here reported that callus formation was observed by wrapping a polyfluoroethylene electret film around the thigh bone of rabbits (Fukada et al., Jpn. J. Appl. Phys. 14, 1975, 2079); that callus was successfully formed by wrapping a poly-γ-methyl L-glutamate piezoelectric film around the thigh bone of rabbits; and that callus formation was observed by wrapping a polyvinylidene fluoride piezoelectric electret film around the thigh bone of monkeys and so on (Fukada, Jpn. J. Appl. Phys., 48 (4), 1979, 381–386). In the above reports, the site where bone production was desired was covered with a piezoelectric sheet and bone production was promoted by electrical stimulus with the piezoelectric sheet.

In the dental field, the guided tissue regeneration technique (GTR technique) has been developed as a means of artificially regenerating periodontium destroyed by periodontal diseases such as alveolar abscesses. In GTR technique, a semi-permeable membrane with a high bioaffinity is used to prevent an epithelial tissue from downwards growing and, on the other hand, promote the activation of periodontal cells and expect the formation of new bone. Thus, it is considered that the the newly formed bone can be attached to the existing bone tissue. The narrowing of the alveolar border caused by bone resorption and bone defects in the jawbone and alveolar bone obstruct prosthesis in dentures and implants. In these cases, it has become possible to promote new bone formation by the GTR method. More particularly, the entry of the epithelial tissue to the area around the implant is prevented by the membrane, and cells and capillary blood vessels are selectively induced and regenerated in the space obtained by the membrane (see Nakamura, the Quintessence, Vol. 9, No. 11, pp. 47–54, 1990). The membrane used in the GTR method is a porous membrane such as a Millipore filter or an expanded polyethylene tetrafluoride membrane (Gore-Tex membrane). Recently, the use of biodegradable polylactic acid membranes has been reviewed.

In the above method wherein a piezoelectric sheet is used, there were the disadvantages that the surgical wound was poorly healed, necrosis or bursting of the epithelial tissue on the membrane was liable to occur, and the bone was slowly formed. The reason is believed that the sheet includes no holes, and so the circulation of the tissue fluid is inhibited and the nutrients necessary for the bone regeneration is difficult to be supplied, although an electrical stimulus can be obtained.

Further, in the above-mentioned GTR method wherein the porous membrane such as a Millipore filter or expanded polyethylene tetrafluoride membrane is used, the membrane only provided a field for the bone regeneration. Therefore, the bone regeneration was slow, a considerably long time was required until healing of the wound (about 18 weeks in the case of dogs), and the patients were suffered from quite a little pain. Furthermore, there were the disadvantages that the bone formation or increased bone production beyond the bone regeneration was difficult even if bone was regenerated, and bone maturation was insufficient.

SUMMARY OF THE INVENTION

The present inventors engaged in intensive studies to remedy the above disadvantages and surprisingly found that when a piezoelectric porous membrane having through-holes of a particular pore size is used, bone can be rapidly regenerated and further even increased production of bone beyond the regeneration is obtained.

Accordingly, the object of the present invention is to provide a bone inducing material comprising a piezoelectric porous membrane having through-holes of a particular pore size.

Other objects and effects of the present invention will be clear from the following description.

The present invention relates to a bone inducing material comprising a piezoelectric porous membrane having through-holes of an average pore size of about 0.1 to 5 μm.

The bone inducing material of the present invention is used preferably in the field of dentistry or orthopaedic surgery, more preferably in the treatment of periodontal diseases by the GTR method.

BRIEF DESCRIPTION OF THE DRAWINGS

FIG. 3 and FIG. 4 are adjusted so that the magnifications of the two were the same.

DESCRIPTION OF THE PREFERRED EMBODIMENTS

The piezoelectric porous membrane used as the bone inducing material of the present invention has through-holes of an average pore size of about 0.1 to 5 μm. The average pore size of the through-holes is preferably about 0.2 to 5 μm. The term "through-hole" means an open hole having small pore size or hole composed of a pipe structure and substantially connecting the front and rear surfaces of a membrane. By virtue of the through-hole having such a pore size, it is possible to prevent the epithelial tissue or fibroblast cells which would have a detrimental effect on bone formation, from entering into the space formed by the piezoelectric porous membrane, while allowing impregnation of the tissue fluid necessary for bone formation, and therefore, the bone formation is effectively promoted. If the average pore size is less than about 0.1 μm, there occurs necrosis of the tissue, because the impregnation of the tissue fluid is too small. Further, if the average pore size is greater than about 5 μm, the epithelial tissue and/or fibroblast cells enter and therefore bone cannot be effectively grown. The porosity of the piezoelectric porous membrane is not particularly limited, but is preferably about 40 to 90%, more preferably about 60 to 80%. The above-mentioned piezoelectric porous membrane is composed of a piezoelectric polymer material or a composite material comprising a polymer material and piezoelectric inorganic particle material.

The piezoelectric polymer material is an organic polymer material to which a piezoelectric characteristic is imparted by a polarization treatment. Examples of the piezoelectric polymer material which may be preferably used are a copolymer of vinylidene cyanide-vinyl acetate or polyamide resin having relatively high heat resistance. Further, a polyvinylidene fluoride (PVDF) resin having a high piezoelectric characteristic is preferable. More particularly, in comparison with a vinylidene fluoride (VDF) homopolymer, which requires, when forming the membrane therefrom, a strong solvent or uniaxial stretching so as to obtain the β-type crystallization suitable for appearance of the piezoelectric characteristic, a VDF copolymer capable of obtaining β-type crystallization under normal crystallization conditions, for example, a copolymer of a major amount of VDF and a minor amount of vinyl fluoride, trifluoroethylene (TrFE), tetrafluoroethylene, trifluorochloroethylene, hexafluoropropylene or the like, is preferably used. A copolymer of a major amount, in particular 70 to 80 molar % of VDF and a minor amount, in particular 30 to 20 molar % of TrFE is more preferably used. Further, a copolymer mainly comprising polylactic acid or lactic acid may be used as the piezoelectric polymer material. L-lactic acid is preferable as the lactic acid. As the copolymer mainly comprising lactic acid, a lactic acid/ε-caprolactone copolymer or a lactic acid/glycolic acid copolymer is preferable. The copolymer mainly comprising polylactic acid or lactic acid is preferable, because it may be decomposed in a living body and therefore does not require surgery for removal after the treatment. A lactic acid copolymer is particularly preferable, because the rate of decomposition in a living body can be adjusted.

The composite material comprising the polymer material and piezoelectric inorganic particle materials has a structure wherein the latter materials are dispersed in the former material. As the polymer material, an organic polymer material to which a piezoelectric characteristic cannot be imparted even by a polarization treatment, for example, a polytetrafluoroethylene resin or polypropylene resin may be used, but the above-mentioned piezoelectric polymer material is preferably used. Examples of the piezoelectric inorganic particle materials are particle materials to which a piezoelectric characteristic can be imparted by a polarization treatment, for example, ceramic ferroelectrics, such as PZT ceramics, barium titanate, or a mixture of lead titanate and lead zirconate. Lead Zirconate Titanate (PZT) ceramics or barium titanate is preferable. The size of the particle materials is preferably not more than 100 μm. The ratio (v/v) of the particle materials to the polymer material in the composite material is preferably 0.1 to 1, more preferably 0.2 to 0.7.

The thickness of the piezoelectric porous membrane varies depending on the application site, but is preferably 1 to 600 μm, more preferably 10 to 200 μm, when used for treatment of periodontal diseases. The shape of the piezoelectric porous membrane may also be any suitable shape in accordance with the application site, including, but not limited to, a film, sheet, tube, circle, square, triangle, ovoid, horseshoe, semicircle, or spirally wrapped rod. Further, it may be a shape composed of a collar portion and a skirt portion as that of the commercially available Gore-Tex membrane.

A piezoelectric porous membrane containing many through-holes having a particular pore size may be prepared by combining the conventional methods for forming a porous polymer membrane and a polarization treatment. The conventional methods for forming through-holes are as follows:

(1) A dry method which comprises dissolving the polymer material in a mixture of a good solvent and a poor solvent miscible with the good solvent, casting the resulting solution on a substrate to a certain thickness, and then removing the solvent by evaporation under carefully controlled conditions.

(2) A wet method which comprises dissolving the polymer material in a good solvent, casting the resulting solution on a substrate to a certain thickness, and then solidifying the polymer material in a poor solvent.

(3) A method which comprises dissolving the polymer material in a suitable solvent and then lyophilizing the solution.

(4) The method which comprises drawing the membrane under specific conditions.

(5) A method which comprises irradiating the polymer material with radioactive rays, electron beams, or high energy charged particle materials to form radiation damage and enlarging the formed pores by chemical etching or the like.

(6) A method which comprises incorporating an elutable material in the polymer material and then removing the elutable material after membrane formation.

(7) A method which comprises punching holes in the membrane mechanically by a punch or the like.

(8) A method which comprises punching holes in the membrane by heat or an ultraviolet laser.

Of the above methods, the wet method is preferably used, because the wet method is particularly simple and a porous membrane with desired properties can be prepared at a thickness of 10 to 200 μm with good reproducibility. Further, the porous membranes prepared by the method (1), (2), (4) or (6) has knitted-type structure wherein many fine fibrous materials are combined and complicatedly entangled with each other, and continuous voids (through-holes) are formed between the fibrous materials.

The good solvent for a PVDF resin may be any solvent which can dissolve the resin in a concentration suitable for forming a coating membrane, for example, a polar organic solvent such as dimethylacetoamide (DMA), dimethylformamide (DMF), hexamethylphosphoric acid triamide (HMPTA), acetone, methylethylketone, dimethylsulfoxide, cyclohexanone. For VDF homopolymer, a strong solvent such as DMA, DMF or HMPTA is preferably used to obtain the β-type crystallization. Further, water is a preferred poor solvent, but other poor solvents such as methanol or ethanol may be used. The poor solvent of choice must be miscible with the good solvent used.

The polarization treatment may be performed before, during or after the above-mentioned procedure for formation of through-holes. Polarization treatment after the formation of the through-holes, that is, polarization treatment of a porous material, was considered difficult because the electric field is sometimes not effectively applied due to air discharge or dielectric breakdown easily occurs. However, this problem has been solved by the process developed by the present inventors and the co-workers. The process comprises carrying out polarization treatment while sandwiching the porous membrane between dielectric membranes.

As the above method (6) of forming through-holes, the method described, for example, in Japanese Examined Patent Publication No. 2-19984 may be used. The Publication No. 2-19984 discloses a method of production of a polymer complex porous piezoelectric material by mixing a polymer material, piezoelectric inorganic particle materials, organic liquid and inorganic particle materials to produce solution, forming a shaped product, performing polarization treatment, and then extracting the organic liquid and the inorganic particle materials from the shaped product. In the methods (7) and (8) of forming through-holes, it is possible to perform the polarization treatment before the formation of the through-holes.

The polarization treatment may be performed by, for example, attaching suitable electrodes to the two surfaces of the membrane prepared by the above methods, applying a DC voltage of 10 to 3000 kV/cm at room temperature to 200° C., and then gradually cooling to room temperature. The piezoelectric constant ($d_h$ constant) of the piezoelectric porous membrane used in the present invention is preferably 0.1 to 100 pC/N (picocoulomb/newton), more preferably 0.2 to 50 pC/N. If the piezoelectric constant is less than 0.1 pC/N, the bone formation becomes too slow.

As explained above, the present inventors and the co-workers invented a process of preparing a piezoelectric porous membrane comprising subjecting a polarization treatment to a porous membrane sandwiched between dielectric sheets. In the above process, it is preferable to impregnate the porous membrane with an insulating oil in advance and remove the insulating oil after the polarization treatment. According to the process of polarization treatment found by the present inventors and the co-workers, dielectric breakdown hardly occurs in the charging space and the potential charged to the porous membrane surface can be increased, due to the presence of the dielectric sheets. When needle electrodes are used, polarization can be effectively performed, because penetration of air ionized by corona discharge treatment into the porous membrane is prevented, and thus, dielectric breakdown hardly occurs. Further, when plate electrodes are used, poor contact between the electrodes and the porous membrane and heterogeneity of the electric field are reduced due to the potential division caused by the dielectric sheets. As a result, it is possible to apply a sufficient electric field necessary for expressing the piezoelectric characteristic to the porous membrane material and obtain a porous piezoelectric membrane with a superior piezoelectric characteristic. Further, if the porous membrane is impregnated with an insulating oil in advance, it is possible to further increase the potential charged and easily obtain a more preferable porous piezoelectric membrane. The insulating oil can be removed by drying the porous membrane after the polarization. The above process is particularly useful when a porous membrane composed of a polymer piezoelectric material is treated.

As the dielectric sheet, a sheet which is electrically insulating and has heat resistance and potential resistance may be used. The dielectric sheet are composed of, for example, olefinic resin such as polyethylene, polypropylene or α-polyolefin, or synthetic resin such as polyester, polystyrene, polyvinylidene fluoride, polycarbonate, polyethylene tetrafluoride, polyphenylene sulfide, polyvinylchloride, polyvinylidene chloride, copolymers or blended shaped articles of two or more of the above polymers, or nonpolar glass. Of the above sheets, a dielectric sheet having 1/100 to 100, preferably the same extent (1/10 to 10) in a resistance ratio of the dielectric sheet to the porous membrane in the direction of thickness thereof is preferably used. Further, the thickness of the dielectric sheet is approximately the same as or 1/10 the thickness of the porous membrane so as not to cause a potential drop.

As the examples of the insulating oil, there may be mentioned oils which is non-flammable, in a liquid state at ordinary temperature, does not have a high boiling point, and can be easily dried and removed, for example, fluorocarbons such as trichlorotrifluoroethane, tetrachlorodifluoroethane, dibromotetrafluoroethane, trichloromonofluoromethane, perfluoroheptane, perfluorohexane or perfluorooctane, perfluoropolyethers, or fluoroalcohols such as pentafluoropropanol. An insulating oil having a dielectric strength of at least 10 kV, preferably at least 25 kV at 25° C. and 2.54 mm gap is preferably used.

The present invention provides a new technology that a polymer piezoelectric porous membrane is applied to bone formation for the first time. The bone inducing material of the present invention can be used for the regeneration and/or new formation of any bone in a similar manner to the similar bone inducing materials of the prior art, in particular, can be used in a similar manner to the conventional semi-permeable membrane in the GTR method in the dentistry field. More particularly, when the bone inducing material of the present invention is placed at a site where the bone is to be regenerated and/or newly formed, an electrical stimulus is given to the bone to promote the bone formation, and the components necessary for bone formation is supplied to the site of bone formation, whereas components which are not desirable to exist at the site of bone formation can be eliminated. For example, when the periodontal disease is treated by the GTR method in the dentistry field, the bone inducing material of the present invention is implanted between the gingival epithelial tissue and the alveolar bone, whereby deep penetration and proliferation of cells of the gingival connective tissue and the epithelial tissue in the periodontal tissue are inhibited and the regeneration of the cementum, periodontal ligament, and alveolar bone is promoted. Further, the bone inducing material of the present invention may also be applied to areas around bone implants.

EXAMPLES

The present invention now will be further illustrated by, but is by no means limited to, the following Examples.

Reference Example

Preparation of VDF/TrFE Copolymer Porous Membrane and VDF/TrFE Copolymer Piezoelectric Porous Membrane (1) The following characteristics were evaluated for the porous membranes and piezoelectric porous membranes prepared in this Reference Example:

Piezoelectric constant: The $d_h$ constant was measured by the following method. First, electrodes were formed on the two surfaces of a porous membrane after polarization, using an electroconductive spray paint (made by Shinto Chemitron, Shintron E-63) and repeatedly coating and drying until the surface electrical resistance became not more than 10 ohm/ . Then, the membrane was cut out to a sample of 1.5 cm×2 cm, and the sample was immersed in silicone oil filled in a pressure-resistant container. The charge Q [coulomb (C)] of the sample was measured while adding pressure P [newton (N)/m$^2$] from a nitrogen gas source to the container. The increased amount dQ of the charge with respect to the pressure rise dP around the gauge pressure of 2 kgf/cm$^2$ was determined and the following equation was used to calculate:

$$d_h = (dQ/dP)/A$$

The unit is C/N, and A is the electrode area (m$^2$). The $d_h$ constant of the piezoelectric material of the present Reference Example was a negative value, but in the present invention, only the magnitude is shown by an absolute value.

Porosity: Porosity is the ratio (percentage) of voids in the apparent volume of the porous membrane and was determined by calculation from the weight of the membrane and the density of the individual polymers.

Average pore size: The size was determined from an electron microscope photograph of the surface of the porous membrane.

(2) A VDF/TrFE (75/25 molar ratio) copolymer (Kureha Chemical Industry Co.) was stirred and dissolved in an acetone solution at ordinary temperature to obtain a 5% by weight polymer solution. The solution was cast over a glass plate, then the plate was immersed for 30 minutes in a water bath and dried to obtain a VDF/TrFE copolymer porous membrane (thickness=130 μm; porosity=70%, average pore size=0.45 μm).

The intrinsic viscosity of the copolymer used was 3.0 dl/g as a DMF solution of 0.4 g/dl polymer at 30° C.

A transparent membrane obtained by not extracting or replacing the solvent after the casting, but by only drying had a β-type crystallization ratio of 92%, determined from the ratio of absorbance at the absorption wavelength of 538 $cm^{-1}$ for the α-type crystal and absorbance at the absorption wavelength 510 $cm^{-1}$ for the β-type crystal, in an infrared absorption spectrum. The above result shows that the porous membrane similarly had substantially the β-type crystal structure.

(3) The resulting porous membrane was cut to a size of 10 cm×10 cm and impregnated with perfluoropolyether oil (boiling point=97° C., insulation=40 kV at 25° C./2.54 mm gap) as an insulating oil, and sandwiched on its two sides by a PVDF monoaxially drawn sheet (thickness 30 μm) to form a sandwich membrane.

On one side of the sandwich membrane, a tin foil electrode (negative electrode; 8 cm×8cm) was placed in close contact. Needle electrodes (positive electrodes) were disposed facing the other surface. The distance between electrodes was 1 cm. Polarization treatment was performed by corona charging at room temperature. The corona charging was performed for 50 seconds at an output voltage of 35 kV using a high potential power source (made by Pulse Denshi Co., HDV-100K3SS).

Then, the porous membrane was dried in a vacuum and the perfluoropolyether oil was removed to obtain a VDF/TrFE copolymer piezoelectric porous membrane [piezoelectric constant ($d_h$ constant)=2.1 pC/N, thickness=130 μm; porosity=70%; average pore size=0.45 μm].

(4) The procedure described in the above (3) was repeated, except that an insulating oil was not used and the charge was maintained for 50 seconds at an output voltage of 14 kV, to obtain a VDF/TrFE copolymer piezoelectric porous membrane [piezoelectric constant ($d_h$ constant)=0.69 pC/N, thickness=130 μm; porosity=70%; average pore size=0.45 μm].

Example 1

Effect of Bone Inducing Material (VDF/TrFE Copolymer Piezoelectric Porous Membrane)

As the bone inducing material of the present invention, the VDF/TrFE copolymer piezoelectric porous membrane prepared in the above Reference Example 1(3) (average diameter=0.45 μm; porosity=70%, thickness=130 μm, piezoelectric constant=2.1 pC/N] was used. A VDF/TrFE copolymer (porosity=70%, average pore size=0.45 μm, thickness=130 μm) with no piezoelectric characteristic was used for a control test.

Three adult beagles were used as the experimental animals. The fore-molars of the two sides of the jawbones were extracted. After three months from the extraction, the healing of the extracted tooth sockets was confirmed. After the mucoperiosteal flaps was peeled, two bone cavities (diameter=4 mm, depth=4 mm) reaching the medullary cavity were formed in the right and left sides, respectively. Of the four bone cavities, two were covered with the above-mentioned VDR/TrFE copolymer piezoelectric porous membrane (the present invention group), one was covered with the above-mentioned VDF/TrFE copolymer (nonpiezoelectric) porous membrane (comparison group), and the remaining one was left as it was without covering (control group). Then, the above experimental groups were covered with the mucoperiosteal flap and sutured.

After six weeks from the surgery, the portions to be examined in the jawbone were excised. Six nondecalcified polished specimens were prepared for each defect, using ordinary methods. The four specimens corresponding to the central portion were histologically studied from microradiograms, fluorescent labeling observation, and conventional staining observation. The following results were obtained:

(1) The amount of bone newly formed at the bone cavities was greatest in the present invention group, followed by the comparison group and the control group. Further, in the present invention group, sustained, active bone formation was observed along the membrane.

(2) In the present invention group, the medullary cavity was covered with newly formed bone in most of the specimens (71%), whereas the medullary cavity was not closed in 50% of both of the specimens of the comparison group and control group.

(3) In the present invention group, increased production of newly formed bone was observed at the top portions of the existing alveolar bone of all the specimens. Whereas no increased production of newly formed bone was observed at all in the top portions of the existing alveolar bone in the comparison group and the control group.

(4) In the present invention group, addition of newly formed bone was observed inside the medullary cavity (facial and lingual sides), whereas in the comparison group and control group, almost no newly formed bone was observed.

Figure 1:
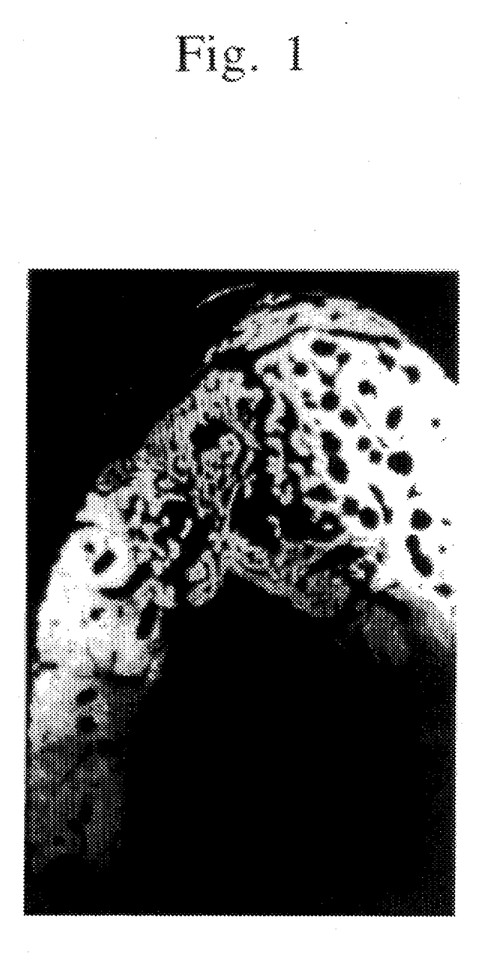
FIG. 1 is a photograph showing a microradiogram of the bucco-lingual sectional view of a mandibula when the bone inducing material of the present invention is used.
Figure 2:
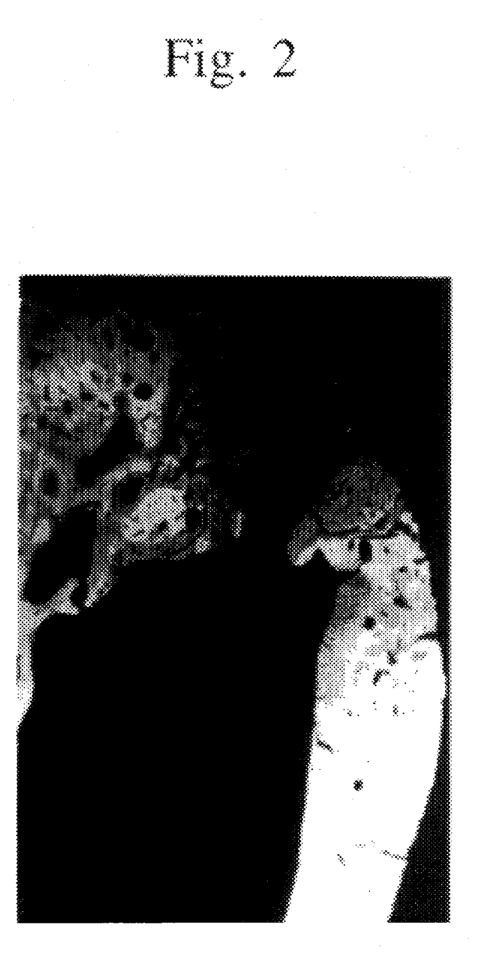
FIG. 2 is a photograph showing a microradiogram of the bucco-lingual sectional view of a mandibula when a porous membrane not having a piezoelectric characteristic is used.
Figure 3:
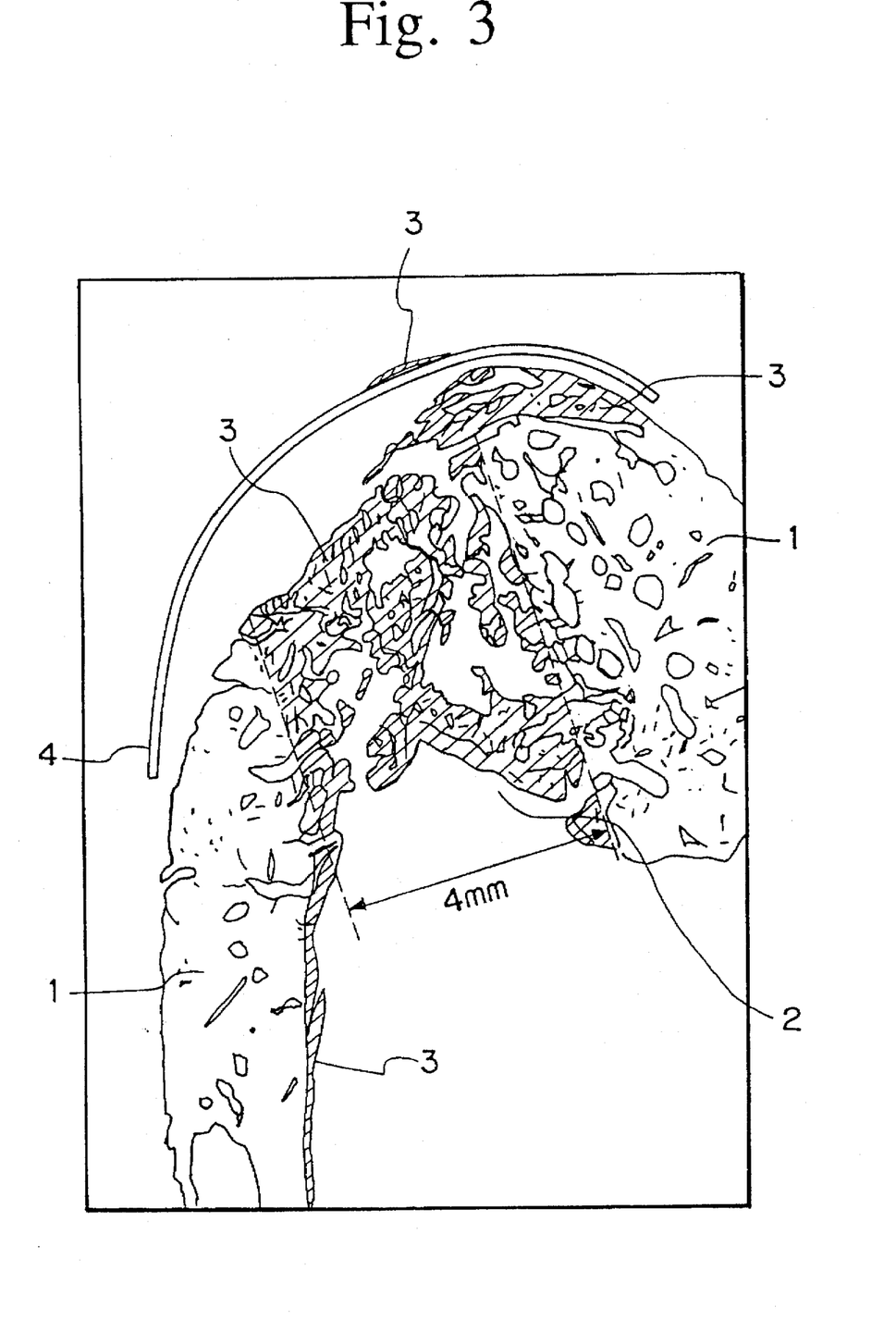
FIG. 3 schematically illustrates a bucco-lingual sectional view of a mandibula, prepared from the photograph of FIG. 1.
Figure 4:
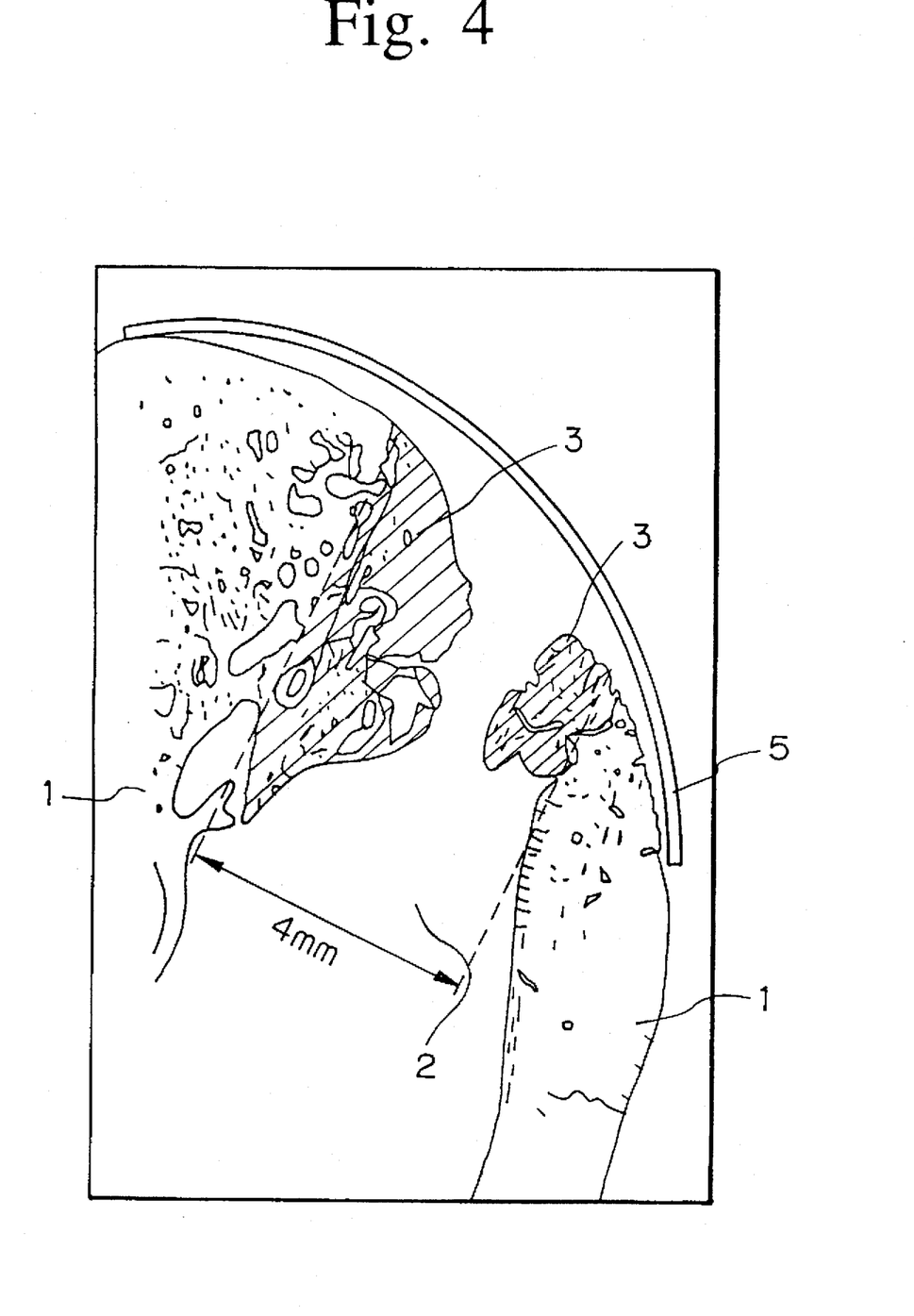
FIG. 4 schematically illustrates a bucco-lingual sectional view of a mandibula, prepared from the photograph of FIG. 2.

Examples of the microradiogram of bucco-lingual sectional views of mandibula of the present invention group and comparison group are shown in FIGS. 1 to 4. In FIGS. 3 and 4, 1 shows the existing bone, 2 shows the bone cavities, 3 shows the newly formed bone, 4 shows the VDR/TrFE copolymer piezoelectric porous membrane, and 5 shows the VDR/TrFE copolymer nonpiezoelectric porous membrane.

Example 2

Effect of Pore Size of VDF/TrFE Copolymer Piezoelectric Porous Membrane

As the VDF/TrFE copolymer piezoelectric porous membrane (thickness=130 μm, piezoelectric constant=2.1 p C/N), three types of piezoelectric porous membranes having average pore sizes of 0.6 μm, 5 μm, and 30 μm were used.

As the experimental animals, nine (9) mix breed dogs (male; body weight=10 to 15 kg) were used. Before the experiment, the second, third, and fourth fore-molars and the first rear-molars in the two sides of the mandibula were extracted. After three months, incisions were made with avoiding the portions to be covered with the membranes, the mucoperiosteal flap was peeled, and four artificial bone cavities of an oval shape of a length of 6.0 mm, a width of 3.3 mm, and a depth of 4.0 mm were formed. The artificial bone cavities at the right side of the mandibula were covered with a piezoelectric porous membrane having an average pore size of 30 μm and a piezoelectric porous membrane having an average pore size of 5 μm, while one of the artificial bone cavities at the left side was covered with a piezoelectric porous membrane of an average pore size of 0.6 μm. Further, the remaining one site was not covered with a membrane and was examined as the control group. The piezoelectric porous membranes were affixed with titanium pins to firmly cover the bone cavities and the area including the portions 3 mm apart from the bone edge, and the mucoperiosteal flaps were sutured tight.

The animals were divided into three groups (three dogs per group) according to the observation period, i.e., an eight week group, 16 week group, and 24 week group. A labeling agent was administered to mark the time of the formation of the bone. After the end of the observation period, the animals were placed under general anesthesia, the head and neck portions were affixed and perfusion was performed with a 10% neutrally buffered formalin solution, then the portions to be examined in the jawbones were excised and histologically examined.

In the case of a VDF/TrFE copolymer piezoelectric porous membrane having an average pore size of 30 μm, the epithelial tissue invaded the inner space covered with the membrane and the regeneration of newly formed bone was insufficient. Whereas, in the case of a VDF/TrFE copolymer piezoelectric porous membrane having 5 μm and 0.6 μm, regeneration and increased production of newly formed bone similar to that of Example 1 were observed.

Example 3

The procedure described in Examples 1 and 2 is repeated, except the VDF/TrFE copolymer piezoelectric porous membrane prepared in the above Reference Example 1(4) is used to obtain a similar effect.

The bone inducing material of the present invention exhibits surprisingly rapid bone formation in comparison with conventional inducing materials and in particular is clinically useful for quick regeneration of alveolar bone. Therefore, the possibility is suggested to application to alveolar border formation techniques.

As above, the present invention was explained with reference to particular embodiments, but modifications and improvements obvious to those skilled in the art are included in the scope of the present invention.

What is claimed is:

1. A bone inducing material consisting essentially of a piezoelectric porous membrane having through-holes of an average pore size of about 0.1 to 5 μm and having porosity, defined as the ration (percentage) of voids in the apparent volume of the piezoelectric porous membrane, of about 40 to 90%, said piezoelectric porous membrane being composed of a piezoelectric polymer material or a composite material comprising a polymer material and piezoelectric inorganic particle materials.

2. A bone inducing material according to claim 1, wherein the piezoelectric polymer material is a polyvinylidene fluoride, a copolymer whose main component is a vinylidene fluoride, a polylactic acid, or a copolymer whose main component is lactic acid.

3. A bone inducing material according to claim 1, wherein the composite material is composed of a piezoelectric polymer material and piezoelectric inorganic particle materials.

4. A bone inducing material according to claim 3, wherein the piezoelectric inorganic particle material is lead zirconate titanate (PZT) ceramics or barium titanate.

5. A bone inducing material according to claim 1, wherein the piezoelectric porous membrane is prepared by polarizing a porous membrane sandwiched between dielectric sheets.

6. A bone inducing material according to claim 1, for inducing bone of periodontium.

7. A method of inducing bone comprising placing a bone inducing material, which consists essentially of a piezoelectric porous membrane having through-holes of an average pore size of about 0.1 to 5 μm and having porosity, defined as the ratio (percentage) of voids in the apparent volume of the piezoelectric porous membrane, of about 40 to 90%, at a site where bone regeneration and/or new formation of bone is required, said piezoelectric porous membrane being composed of a piezoelectric polymer material or a composite material comprising a polymer material and piezoelectric inorganic particle materials.

8. A method of inducing bone according to claim 7, wherein the piezoelectric polymer material is a polyvinylidene fluoride, a copolymer whose main component is vinylidene fluoride, a polylactic acid, or a copolymer whose main component is lactic acid.

* * * * *

UNITED STATES PATENT AND TRADEMARK OFFICE
CERTIFICATE OF CORRECTION

PATENT NO. : 5,684,061
DATED : November 4, 1997
INVENTOR(S) : TOSHIYUKI OHNISHI et al It is certified that error appears in the above-identified patent and that said Letters Patent is hereby corrected as shown below:

In column 10, line 7, change "ration" to --ratio--.

Signed and Sealed this

Twenty-fourth Day of February, 1998

Attest:

BRUCE LEHMAN

Attesting Officer        Commissioner of Patents and Trademarks